United States Patent
Wu

(10) Patent No.: US 10,975,356 B2
(45) Date of Patent: Apr. 13, 2021

(54) METHOD FOR OBTAINING FEMALE GERMLINE STEM CELLS FROM FOLLICULAR ASPIRATES

(71) Applicant: Shanghai Jiaotong University, Shanghai (CN)

(72) Inventor: Ji Wu, Shanghai (CN)

(73) Assignee: Shanghai Jiaotong University, Shanghai (CN)

( * ) Notice: Subject to any disclaimer, the term of this patent is extended or adjusted under 35 U.S.C. 154(b) by 145 days.

(21) Appl. No.: 16/075,586

(22) PCT Filed: Feb. 4, 2016

(86) PCT No.: PCT/CN2016/073429
§ 371 (c)(1),
(2) Date: Aug. 3, 2018

(87) PCT Pub. No.: WO2017/132926
PCT Pub. Date: Aug. 10, 2017

(65) Prior Publication Data
US 2019/0169568 A1  Jun. 6, 2019

(51) Int. Cl.
*C12N 5/071* (2010.01)
*C12N 5/075* (2010.01)
*G01N 33/569* (2006.01)

(52) U.S. Cl.
CPC ......... *C12N 5/0682* (2013.01); *C12N 5/0609* (2013.01); *G01N 33/56966* (2013.01); *C12N 2506/243* (2013.01); *C12N 2509/00* (2013.01); *C12N 2533/54* (2013.01); *C12N 2537/00* (2013.01); *G01N 2333/914* (2013.01)

(58) Field of Classification Search
CPC ................ C12N 5/0682; C12N 5/0609; C12N 2506/243; C12N 2509/00
See application file for complete search history.

(56) References Cited

U.S. PATENT DOCUMENTS

2016/0113680 A1*  4/2016  Hodgson ................ C12M 33/14
600/35

FOREIGN PATENT DOCUMENTS

WO    2009021151 A1    2/2009

OTHER PUBLICATIONS

Yoshida et al. J Reprod Fert 95:481-488, 1992. (Year: 1992).*
Zou et al. 2009 Nature Cell Biology 11(5):631-636. Supplemental Information pp. 1-14 (Year: 2009).*
Zou et al. 2011 Stem Cells and Development 20(12):2197-2204 (Year: 2011).*
White et al. 2012 Nature Medicine 18(3):413-422 (Year: 2012).*
Li et al., "Research progress and application of ovarian germ stem cells," Journal of Dalian Medical University, Mar. 20, 2013, vol. 35, No. 3, pp. 286-289. Abstract only consider.
White Y. A. R. et al. "Oocyte formation by mitotically-active germ cells purified from ovaries 1-13 of reproductive age women" Nat Med., vol. 18, No. 3, Feb. 26, 2012 (Feb. 26, 2012), ISSN: 1078-8956, pp. 413-421.
International Search Report in corresponding PCT Patent Application No. PCT/CN2016/073429, dated Oct. 26, 2016 (2 pages).

* cited by examiner

*Primary Examiner* — Marcia S Noble
(74) *Attorney, Agent, or Firm* — Greenberg Traurig, LLP; Fang Xie

(57) ABSTRACT

Provided is a method for obtaining female germline stem cells from follicular aspirates.

12 Claims, 4 Drawing Sheets
Specification includes a Sequence Listing.

SEQUENCE LISTING

<160> NUMBER OF SEQ ID NOS: 38

<210> SEQ ID NO 1
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 1
cgttgaaatt ctgcgaaaca                                                  20

<210> SEQ ID NO 2
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 2
tctctgttcc cgatcaccat                                                  20

<210> SEQ ID NO 3
<211> LENGTH: 21
<212> TYPE: DNA
<213> ORGANISM: Artificial sequence
<220> FEATURE:
<221> NAME/KEY: misc_feature
<223> OTHER INFORMATION: Primer

<400> SEQUENCE: 3
accatgtcgt ctggtccctg t                                          21

<210> SEQ ID NO 4
<211> LENGTH: 24
<212> TYPE: DNA
<213> ORGANISM: Artificial sequence
<220> FEATURE:
<221> NAME/KEY: misc_feature
<223> OTHER INFORMATION: Primer

<400> SEQUENCE: 4
agcactggga tgacgatgag caga                                       24

<210> SEQ ID NO 5
<211> LENGTH: 18
<212> TYPE: DNA
<213> ORGANISM: Artificial sequence
<220> FEATURE:
<221> NAME/KEY: misc_feature
<223> OTHER INFORMATION: Primer

<400> SEQUENCE: 5
tgagggcgaa gcaggagt                                              18

<210> SEQ ID NO 6
<211> LENGTH: 17
<212> TYPE: DNA
<213> ORGANISM: Artificial sequence
<220> FEATURE:
<221> NAME/KEY: misc_feature
<223> OTHER INFORMATION: Primer

<400> SEQUENCE: 6
tggcgccggt tacagaa                                               17

<210> SEQ ID NO 7
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 7
gttactgggc ggagttcgta                                            20

<210> SEQ ID NO 8
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 8
tgaagtggct tggtgtcttg                                            20

<210> SEQ ID NO 9
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 9
gcccacaacc acgatgaatc                                           20

<210> SEQ ID NO 10
<211> LENGTH: 23
<212> TYPE: DNA
<213> ORGANISM: Artificial sequence
<220> FEATURE:
<221> NAME/KEY: misc_feature
<223> OTHER INFORMATION: Primer

<400> SEQUENCE: 10
cggaggtaca acatagctcc ttt                                       23

<210> SEQ ID NO 11
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 11
gggtgcagcc tttatgagtc                                           20

<210> SEQ ID NO 12
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 12
ccttgttcat gccctgagat                                           20

<210> SEQ ID NO 13
<211> LENGTH: 23
<212> TYPE: DNA
<213> ORGANISM: Artificial sequence
<220> FEATURE:
<221> NAME/KEY: misc_feature
<223> OTHER INFORMATION: Primer

<400> SEQUENCE: 13
actctcagtc tgatctcata gcc                                       23

<210> SEQ ID NO 14
<211> LENGTH: 21
<212> TYPE: DNA
<213> ORGANISM: Artificial sequence
<220> FEATURE:
<221> NAME/KEY: misc_feature
<223> OTHER INFORMATION: Primer

<400> SEQUENCE: 14
taccaagggg aggaaccatt c                                         21

<210> SEQ ID NO 15
<211> LENGTH: 22
<212> TYPE: DNA
<213> ORGANISM: Artificial sequence
<220> FEATURE:
<221> NAME/KEY: misc_feature
<223> OTHER INFORMATION: Primer

<400> SEQUENCE: 15
tcagagccag agattgaaaa ca                                                    22

<210> SEQ ID NO 16
<211> LENGTH: 23
<212> TYPE: DNA
<213> ORGANISM: Artificial sequence
<220> FEATURE:
<221> NAME/KEY: misc_feature
<223> OTHER INFORMATION: Primer

<400> SEQUENCE: 16
ttgcaacata gccatttctt ttt                                                   23

<210> SEQ ID NO 17
<211> LENGTH: 19
<212> TYPE: DNA
<213> ORGANISM: Artificial sequence
<220> FEATURE:
<221> NAME/KEY: misc_feature
<223> OTHER INFORMATION: Primer

<400> SEQUENCE: 17
ggcatgctcc aatgtgtgg                                                        19

<210> SEQ ID NO 18
<211> LENGTH: 19
<212> TYPE: DNA
<213> ORGANISM: Artificial sequence
<220> FEATURE:
<221> NAME/KEY: misc_feature
<223> OTHER INFORMATION: Primer

<400> SEQUENCE: 18
ggtgtgggga tggatttgc                                                        19

<210> SEQ ID NO 19
<211> LENGTH: 19
<212> TYPE: DNA
<213> ORGANISM: Artificial sequence
<220> FEATURE:
<221> NAME/KEY: misc_feature
<223> OTHER INFORMATION: Primer

<400> SEQUENCE: 19
ggcaagacag ctgtcaaga                                                        19

<210> SEQ ID NO 20
<211> LENGTH: 22
<212> TYPE: DNA
<213> ORGANISM: Artificial sequence
<220> FEATURE:
<221> NAME/KEY: misc_feature
<223> OTHER INFORMATION: Primer

<400> SEQUENCE: 20
ttggggagat aatttcagtc gt                                                    22

<210> SEQ ID NO 21
<211> LENGTH: 21
<212> TYPE: DNA
<213> ORGANISM: Artificial sequence
<220> FEATURE:
<221> NAME/KEY: misc_feature
<223> OTHER INFORMATION: Primer

<400> SEQUENCE: 21

```
atggcacgtc ccaacaaatt c                                              21
```

<210> SEQ ID NO 22
<211> LENGTH: 21
<212> TYPE: DNA
<213> ORGANISM: Artificial sequence
<220> FEATURE:
<221> NAME/KEY: misc_feature
<223> OTHER INFORMATION: Primer

<400> SEQUENCE: 22

```
actcagcact agcagcaatc t                                              21
```

<210> SEQ ID NO 23
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 23

```
tgcaagagtg tgctagaggc                                                20
```

<210> SEQ ID NO 24
<211> LENGTH: 21
<212> TYPE: DNA
<213> ORGANISM: Artificial sequence
<220> FEATURE:
<221> NAME/KEY: misc_feature
<223> OTHER INFORMATION: Primer

<400> SEQUENCE: 24

```
acaaagcagt ccacgaggta g                                              21
```

<210> SEQ ID NO 25
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 25

```
cgccatgttc tctgtctcaa                                                20
```

<210> SEQ ID NO 26
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 26

```
cgtttgttca catcccagtg                                                20
```

<210> SEQ ID NO 27
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 27
gcctcccagg acccattctc                                          20

<210> SEQ ID NO 28
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 28
caggtagcag atggagccta                                          20

<210> SEQ ID NO 29
<211> LENGTH: 24
<212> TYPE: DNA
<213> ORGANISM: Artificial sequence
<220> FEATURE:
<221> NAME/KEY: misc_feature
<223> OTHER INFORMATION: Primer

<400> SEQUENCE: 29
agcaggaccc agatgaactc aaca                                     24

<210> SEQ ID NO 30
<211> LENGTH: 24
<212> TYPE: DNA
<213> ORGANISM: Artificial sequence
<220> FEATURE:
<221> NAME/KEY: misc_feature
<223> OTHER INFORMATION: Primer

<400> SEQUENCE: 30
aagcccactg ctctacttca tggt                                     24

<210> SEQ ID NO 31
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 31
cagaaggcct cagcacctac                                          20

<210> SEQ ID NO 32
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 32
ctgttccagg cctgattgtt                                          20

<210> SEQ ID NO 33
<211> LENGTH: 19
<212> TYPE: DNA
<213> ORGANISM: Artificial sequence
<220> FEATURE:
<221> NAME/KEY: misc_feature
<223> OTHER INFORMATION: Primer

<400> SEQUENCE: 33
atgcaccgct acgacgtga                                           19

<210> SEQ ID NO 34
<211> LENGTH: 20
<212> TYPE: DNA
<213> ORGANISM: Artificial sequence
<220> FEATURE:
<221> NAME/KEY: misc_feature
<223> OTHER INFORMATION: Primer

<400> SEQUENCE: 34
cttttgcacc cctcccattt                                          20

<210> SEQ ID NO 35
<211> LENGTH: 24
<212> TYPE: DNA
<213> ORGANISM: Artificial sequence
<220> FEATURE:
<221> NAME/KEY: misc_feature
<223> OTHER INFORMATION: Primer

<400> SEQUENCE: 35
cagatcctaa acagctcgca gaat                                     24

<210> SEQ ID NO 36
<211> LENGTH: 23
<212> TYPE: DNA
<213> ORGANISM: Artificial sequence
<220> FEATURE:
<221> NAME/KEY: misc_feature
<223> OTHER INFORMATION: Primer

<400> SEQUENCE: 36
gcgtacgcaa attaaagtcc aga                                      23

<210> SEQ ID NO 37
<211> LENGTH: 22
<212> TYPE: DNA
<213> ORGANISM: Artificial sequence
<220> FEATURE:
<221> NAME/KEY: misc_feature
<223> OTHER INFORMATION: Primer

<400> SEQUENCE: 37
gacatcaaga aggtggtgaa gc                                       22

<210> SEQ ID NO 38
<211> LENGTH: 22
<212> TYPE: DNA
<213> ORGANISM: Artificial sequence
<220> FEATURE:
<221> NAME/KEY: misc_feature
<223> OTHER INFORMATION: Primer

<400> SEQUENCE: 38
gtccaccacc ctgttgctgt ag                                       22

METHOD FOR OBTAINING FEMALE GERMLINE STEM CELLS FROM FOLLICULAR ASPIRATES

CROSS REFERENCE TO RELATED APPLICATIONS

This application is a U.S. National Phase application under 35 U.S.C. 371 of International Application No. PCT/CN2016/073429, filed Feb. 4, 2016, the disclosure of which is incorporated herein by reference in its entirety.

TECHNICAL FIELD

The present invention belongs to the field of infertility and fertility preservation; more specifically, the present invention relates to a method for obtaining female germline stem cells from follicular aspirates.

BACKGROUND ART

Epidemiological statistics have found that about 48.5 million couples worldwide face infertility problems every year (Mascarenhas, M. N., S. R. Flaxman, T. Boerma, et al., National, Regional, and Global Trends in Infertility Prevalence Since 1990: A Systematic Analysis of 277 Health Surveys. PLoS Med, 2012. 9(12): p. e1001356). Infertility has become a major health and social problem. Germline stem cells can be used to study the pathogenesis of infertility. The present inventors have isolated female germline stem cells (FGSCs) from postnatal mouse ovaries for the first time in the world. A C-terminal DDX4 antibody is used for magnetic bead sorting of germ cells from the postnatal mouse ovaries. The germ cells can be used to establish FGSC cell lines after in vitro culture. Transplantation of FGSCs into the infertile mouse ovaries may produce functional oocytes and offspring (Zou, K., Z. Yuan, Z. Yang, et al., Production of offspring from a germline stem cell line derived from neonatal ovaries. Nat Cell Biol, 2009. 11(5): p. 631-636). Subsequently, White et al. used the same antibody to flow-sort human FGSCs from ovaries of women of childbearing age (White, Y.A.R., D. C. Woods, Y. Takai, et al., Oocyte formation by mitotically active germ cells purified from ovaries of reproductive-age women. Nat Med, 2012. 18 (3): p. 413-421). An increasing number of studies have found that there are FGSCs in mouse, rat and human ovaries. It is worth mentioning that the latest clinical studies have found that injecting mitochondria of human FGSCs into the patient's own oocytes can improve the quality of oocytes and increase the success rate of in vitro fertilization (IVF) (Fakih, M. H., M. E. Shmoury, J. Szeptycki, et al., The AUGMENT$^{SM}$ Treatment: Physician Reported Outcomes of the Initial Global Patient Experience. JFIV Reprod Med Genet 2015. 3 (3): p. 154).

FGSCs have a variety of clinical application values, including the treatment of female infertility, preservation of female fertility, and postponement of female menopause. However, ovarian tissues can be clinically obtained only in three ways: during the caesarean section, during the laparoscopy in infertility examination, and during the ovariectomy in the treatment of various gynecological diseases. Since the ovary is located in the abdominal cavity, ovarian tissues are mainly obtained by laparotomy and laparoscopy. This restricts the clinical application of FGSCs.

Human FGSCs have opened up new ideas for postponing female menopause, treating female infertility, and providing fertility preservation methods. However, the shortage of human ovarian tissues restricts the future research and clinical applications of human FGSCs. This shortage prompts people to find alternative sources of FGSCs. Assisted Reproductive Technology (ART) is a widely used medical technology. International Committee Monitoring Assisted Reproductive Technologies has reported that at least 1 million cases are implemented every year worldwide to help infertile couples to obtain offspring. In ART, transvaginal ultrasound-guided follicular puncture and aspiration is a commonly used technique for collecting oocytes, and follicular aspirates are produced during this operation.

After picking out mature oocytes, the follicular aspirates are often discarded, resulting in a very serious waste of clinical resources. Previous reports have found that preantral follicles can be obtained from follicular aspirates, and oocytes can be obtained after in vitro culture of these preantral follicles (Wu, J., L. Z. Zhang and P. Liu, A new source of human oocytes: preliminary report on the identification and maturation of human preantral follicles from follicular aspirates. Human Reproduction, 1998. 13(9): p. 2561-2563). However, no literature has currently reported that follicular aspirates contain ovarian tissues from which FGSCs can be obtained.

SUMMARY OF THE INVENTION

The object of the present invention is to provide a method for obtaining female germline stem cells from follicular aspirates. Preferably, the female germline stem cells are human female germline stem cells.

In a first aspect of the present invention, provided is a method for separating female germline stem cells from follicular aspirates, comprising:

(1) separating ovarian tissues or cell masses from the follicular aspirates and performing cell dispersion to obtain single cells; and (2) inoculating and culturing the cells obtained in step (1) on inactivated feeder layer cells, and sorting female germline stem cell marker-positive cells from the cultured cells.

In one preferred embodiment, the follicular aspirates are follicular aspirates from at least one donor.

In another preferred embodiment, the follicular aspirates are clinically discarded follicular aspirates.

In another preferred embodiment, the method further comprises the following step: (3) proliferation-culturing and subculturing the female germline stem cell marker-positive cells obtained in step (2) on feeder layer cells; preferably, proliferation-culturing and subculturing same in a stem cell culture medium.

In another preferred embodiment, in step (1), the method for separating the ovarian tissues or cell masses from the follicular aspirates comprises: filtering the follicular aspirates by using a cell strainer with a pore size of 30-100 μm, with solids retained on the strainer as the ovarian tissues or cell masses.

In another preferred embodiment, the solids retained on the strainer as the ovarian tissues or cell masses are separated from the strainer (preferably, the strainer is washed with sterile PBS buffer), and the ovarian tissues or cell masses are separated from the follicular aspirates by the method of centrifugation.

In another preferred embodiment, centrifugation is performed at 300 g for 5 minutes, the supernatant is discarded, and solid-phase cell masses are collected.

In another preferred embodiment, in step (1), before performing the cell dispersion, the method further comprises: further treating the obtained ovarian tissues or cell masses to remove red blood cells.

In another preferred embodiment, the solids retained on the strainer are rinsed to remove red blood cells when filtering the follicular aspirates by using a cell strainer; or alternatively, the red blood cells are lysed and removed by using a red blood cell lysis solution.

In another preferred embodiment, PBS buffer is used as a rinse solution when rinsing the solids retained on the strainer; preferably, rinsing until there are no visible blood cells.

In another preferred embodiment, in step (1), the cell dispersion (i.e., digestion of the tissues or cell masses into single cells) is performed by using one or more enzymes selected from the group consisting of collagenase IV, trypsin, trypsin substitute (TrypleE™ Express) or Acutase™.

In another preferred embodiment, the cell dispersion is performed using collagenase IV, trypsin and EDTA. Preferably, the ovarian tissues or cell masses are placed in PBS containing 1±0.5 mg/mL collagenase IV, and then slowly shaken for 5±3 minutes in a water bath at 37° C.±1° C. The solution is centrifuged at 300 g for 5 minutes, washed with PBS buffer and centrifuged again. PBS containing 0.5 mM EDTA and 0.05% trypsin is added to the centrifuge tube, and the centrifuge tube is slowly shaken for 2-3 minutes in a water bath at 37° C.±1° C. Serum is used to stop the action of trypsin when most cells are dispersed.

In another preferred embodiment, in step (2), the feeder layer cells include STO cells, MEF cells or SNL cells.

In another preferred embodiment, the inactivated feeder layer cells in step (2) are mitomycin C-inactivated feeder layer cells; or the culture period on the feeder layer cells is 10-18 days in step (2).

In another preferred embodiment, in step (2), an antibody specific to a female germline stem cell marker is conjugated to magnetic beads and incubated with the cells cultured on the feeder layer cells in order to sort the female germline stem cell marker-positive cells.

In another preferred embodiment, the inactivated feeder layer cells are obtained as follows: the feeder layer cells are treated with mitomycin C (preferably treated at 10 μg/mL for 2.5±0.5 hours), digested into single cells after washing, and inoculated on a gelatin-coated cell culture plate.

In another preferred embodiment, the female germline stem cell marker includes: DDX4 (DEAD box polypeptide 4) and IFITM3 (interferon-induced transmembrane protein 3); preferably, DDX4.

In another aspect of the present invention, provided is a method for obtaining ovarian tissues or cell masses, comprising: separating the ovarian tissues or cell masses from follicular aspirates.

In one preferred embodiment, the method comprises: filtering the follicular aspirates by using a cell strainer with a pore size of 30-100 μm, with solids retained on the strainer as the ovarian tissues or cell masses.

Other aspects of the present invention will be apparent to those skilled in the art from the disclosure herein.

DETAILED DESCRIPTION OF EMBODIMENTS

Female germline stem cells (FGSCs) are a kind of germline stem cells present in the ovaries and have a variety of clinical application values. The present inventors have discovered for the first time in the study that follicular aspirates comprise ovarian tissues or cell masses from which female germline stem cells can be obtained.

As used herein, the "follicular aspirates" are follicular aspirates clinically produced by follicular puncture and aspiration. In general, oocyte-containing aspirates can be obtained after clinical follicular puncture and aspiration (e.g., oocyte retrieval via transvaginal ovarian puncture). The "follicular aspirates" of the present invention are usually follicular aspirates remained after picking out mature oocytes. The follicular aspirates can also be wastes generated when transvaginal ultrasound-guided follicular puncture and aspiration is used to treat benign ovarian cysts (Katayama, K. P., M. Roesler, C. Gunnarson, et al., Ultrasound-guided transvaginal needle aspiration of follicles for in vitro fertilization. Obstetrics and Gynecology, 1988. 72(2): p. 271-274; and Nikolaou, M., G Adonakis, P. Zyli, et al., Transvaginal ultrasound-guided aspiration of benign ovarian cysts. Journal of Obstetrics and Gynaecology, 2014. 34(4): p. 332-335). The follicular aspirates can also be wastes generated when ultrasound-guided transvaginal ovarian needle drilling (UTND) is used to treat polycystic ovary syndrome (PCOS) (Badawy, A., M. Khiary, A. Ragab, et al., Ultrasound-guided transvaginal ovarian needle drilling (UTND) for treatment of polycystic ovary syndrome: a randomized controlled trial. Fertility and Sterility, 2009. 91(4): p. 1164-1167).

As used herein, the "female germline stem cell marker" refers to a specific molecule expressed on the surface of female germline stem cells (including transmembrane structures), and female germline stem cells can be identified or sorted with an antibody that specifically binds to the marker. In the present invention, the "female germline stem cell marker" includes but is not limited to DDX4 and IFITM3. Most preferably, DDX4 is selected as the marker for female germline stem cell sorting.

As used herein, the "female germline stem cells (FGSCs)" are mammalian female germline stem cells; preferably human female germline stem cells or non-human primate female germline stem cells.

The present invention provides a method for separating female germline stem cells from follicular aspirates, comprising: (1) separating ovarian tissues or cell masses from the follicular aspirates and performing cell dispersion to obtain single cells; and (2) inoculating and culturing the cells obtained in step (1) on inactivated feeder layer cells, and sorting female germline stem cell marker-positive cells from the cultured cells.

Figure 1:
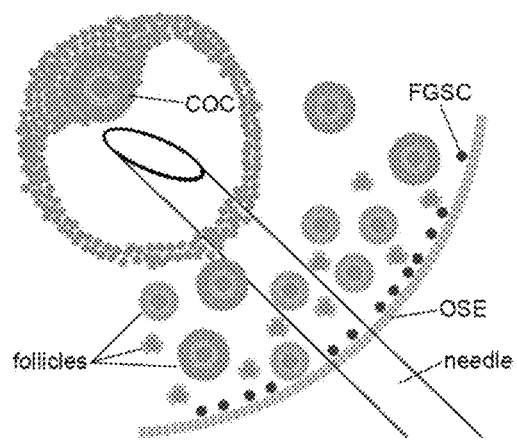
FIG. 1. A schema diagram of obtaining oocytes via transvaginal puncture at an IVF center, showing that preantral follicles and FGSCs can be obtained with mature oocytes.
COC, cumulus-oocyte complexes; and
OSE, ovarian surface epithelium.

The follicular aspirates may be clinically discarded follicular aspirates, such as discarded follicular aspirates obtained after transvaginal puncture and oocyte retrieval at some IVF centers (FIG. 1). That is, the follicular aspirates may be by-products produced from an IVF center. It has been confirmed in the present invention that follicular aspirates contain a small amount of ovarian tissues, and the tissues can be used to obtain female germline stem cells.

The follicular aspirates may be derived from one donor, or may be derived from multiple donors, for example, from 1 to 100 donors, including 2, 5, 10, 20, 40, 60 donors, and so on.

The follicular aspirates can be filtered using a cell strainer with a suitable pore size to obtain valuable ovarian tissues or cell masses from the follicular aspirates. As a preferred embodiment of the present invention, the follicular aspirates are filtered by using a cell strainer with a pore size of 30-100 µm, and solids retained on the strainer serve as the ovarian tissues or cell masses. For example, the pore size of the cell strainer may be 30 µm, 40 µm, 50 µm, 60 µm, 70 µm, 80 µm, 90 µm, or the like.

In order to obtain relatively pure cells and avoid the interference of impurity cells, the step of removing red blood cells in the follicular aspirates is also included during or after the filtration with a strainer. The red blood cells in the follicular aspirates can be removed by rinsing with some commonly used rinse solutions (such as buffers), or the red blood cells can be lysed and removed by using a red blood cell lysis solution. If rinsing is selected to remove the red blood cells, rinsing can be performed during the filtration with a strainer.

The ovarian tissues or cell masses separated from the strainer, preferably also with red blood cells removed, are further centrifuged, the supernatant is discarded, and the ovarian tissues or cell masses at the bottom of the centrifuge tube are collected and ready for subsequent cell dispersion.

The obtained ovarian tissues or cell masses are subjected to cell dispersion to obtain single cells that can be cultured. The cell dispersion can be performed using various physical or chemical methods of cell dispersion well known in the art. As a preferred embodiment of the present invention, the cell dispersion is performed by using one or more enzymes selected from the group consisting of collagenase, trypsin, trypsin substitute (TrypleE™ Express) or Acutase™. As the most preferred embodiment of the present invention, the ovarian tissues are digested into single cells by two-step enzymatic digestion successively comprising: step one, collagenase IV digestion; and step two, trypsin-EDTA digestion. The full name of collagenase is collagen hydrolytic enzyme (collagenase) and it can specifically hydrolyze the three-dimensional helical structure of natural collagen without damaging other proteins and tissues. Collagenase IV comprises at least 7 protease components with molecular weights ranging from 68 to 130 kD. Trypsin is a protease that degrades a protein at a specific site, thus degrading the protein at the juncture between cells. At this time, the cells become spherical due to the tension of their internal cytoskeleton, thereby separating the cells. EDTA is a non-enzymatic digestant, and its mechanism of action is generally believed to be as follows: the adhering and growth of some cells must require the presence of $Ca^{2+}$, while EDTA can form a chelate with $Ca^{2+}$, which can promote the separation of cells.

The obtained single cells are inoculated and cultured on inactivated feeder layer cells. As a preferred embodiment of the present invention, the inactivated feeder layer cells are mitomycin C-inactivated feeder layer cells. As a preferred embodiment of the present invention, the feeder layer cells may include STO cells, MEF cells, SNL cells, or the like.

The culture period on the feeder layer cells is generally 10-18 days, for example, it may be 12, 14, or 16 days. Afterwards, the female germline stem cell marker-positive cells are sorted from the cultured cells.

The female germline stem cell marker is a specific molecule expressed on the surface of female germline stem cells (including transmembrane structures), and female germline stem cells can be identified or sorted with an antibody that specifically binds to the marker. The specific antibody may be a monoclonal antibody or a polyclonal antibody. The female germline stem cell marker can be used to immunize an animal such as rabbit, mouse, rat, etc. to produce a polyclonal antibody; and various adjuvants can be used to enhance the immune response, including but not limited to Freund's adjuvant and the like. Similarly, cells that express a female germline stem cell marker or an antigenic fragment thereof can be used to immunize an animal to produce an antibody. The monoclonal antibody can be prepared using hybridoma technology.

In some embodiments of the present invention, the antibody used for sorting the female germline stem cells may be a C-terminal DDX4 (e.g., available from Abeam, ab13840) antibody, or IFITM3 (e.g., available from Abeam; ab15592) antibody may also be used.

DDX4 or IFITM3 is a female germline stem cell marker, and is also an oocyte marker. Therefore, in fact, the separated cells also contain oocytes when using DDX4 or IFITM3 for cell sorting. However, the present inventors have observed that oocytes cannot survive and proliferate for a long time during the subsequent culture, and gradually disappear. The disappearance of oocytes is also demonstrated in Example 2 of the present invention. The cultured FGSC cell lines do not express the oocyte-related genes C-KIT, FIGLA, GDF9, GJA4, ZP1, ZP2, and ZP3. Therefore, those skilled in the art can understand that DDX4 or IFITM3 can be used as a sorting marker applied in the method of the present invention, and relatively pure FGSC cell lines can also be obtained by the method of the present invention.

An antibody specific to a female germline stem cell marker is conjugated to magnetic beads and incubated with the cells cultured on the feeder layer cells in order to sort the female germline stem cell marker-positive cells. Magnetic beads used for sorting the female germline stem cells may be magnetic beads with a diameter of 2.8 μm (e.g., available from Dynabeads, 112.03 D), or magnetic beads with a diameter of 50 nm (e.g., available from Miltenyi Biotec, 130-048-602) may also be used.

Culture medium for in vitro proliferation of the female germline stem cells may be a culture medium known in the art. As a preferred embodiment of the present invention, the culture medium may be MEMα containing 10% fetal bovine serum, 1 mM sodium pyruvate, 1 mM non-essential amino acids, 2 mM L-glutamine, 0.1 mM β-mercaptoethanol, 10 ng/mL leukemia inhibitory factor, 20 μg/ml transferrin, 5 μg/ml insulin, 60 μM putrescine, 10 ng/mL epidermal growth factor, 40 ng/mL glial cell-derived neurotrophic factor, 1 ng/mL basic fibroblast growth factor and 15 mg/L penicillin. The formulation of the various components mentioned above can properly fluctuate up and down (for example, 30% up and down; preferably 20% up and down; more preferably 10% up and down; and more preferably 5% up and down), which is easily operated by a person skilled in the art.

As a preferred embodiment of the present invention, the female germline stem cells can also be cultured in MEMα containing 10% fetal bovine serum, 1 mM sodium pyruvate, 1 mM non-essential amino acids, 1× concentration of penicillin-streptomycin-glutamine solution, 0.1 mM β-mercaptoethanol, 1× concentration of N–2 supplement, $10^3$ units/ml leukemia inhibitory factor, 10 ng/ml epidermal growth factor, 1 ng/ml basic fibroblast growth factor and 40 ng/ml glial cell-derived neurotrophic factor. The formulation of the various components mentioned above can properly fluctuate up and down (for example, 30% up and down; preferably 20% up and down; more preferably 10% up and down; and more preferably 5% up and down), which is easily operated by a person skilled in the art.

The present inventors have discovered for the first time in the art that follicular aspirates comprise ovarian tissues or cell masses. Based on this new finding of the present inventors, the present invention also provides a method for obtaining ovarian tissues or cell masses, which comprises: separating the ovarian tissues or cell masses from follicular aspirates. As a preferred embodiment of the present invention, the method comprises: filtering the follicular aspirates by using a cell strainer with a pore size of 30-100 μm, with solids retained on the strainer as the ovarian tissues or cell masses.

The excellent effects of the present invention lie in:

(1) discovering for the first time that female germline stem cells can be separated from follicular aspirates, and providing a more preferred method for separating and culturing female germline stem cells; and (2) obtaining female germline stem cells from follicular aspirates not only reduces the surgical risks, but also makes full use of clinical resources, as well as provides a new approach for obtaining female germline stem cells.

The present invention is further illustrated below in combination with particular examples. It should be understood that these examples are only for illustrating the present invention and are not intended to limit the scope of the present invention. The experimental methods that do not specify the specific conditions in the following examples are generally performed in accordance with conventional conditions, such as those described in J. Sambrook et al. (eds.), Molecular Cloning: A Laboratory Manual, 3rd Edition, Science Press, 2002, or in accordance with the conditions recommended by the manufacturer.

EXAMPLE 1

Obtaining a Small Amount of Human Ovarian Tissues from the Follicular Aspirates Produced at an IVF Center 1. Obtaining Human Follicular Aspirates After the informed consent was signed, follicular aspirates were obtained from two IVF centers. Patients were between 30 and 35 years old. After oocytes were picked out, follicular aspirates produced from 2-6 patients were collected in a sterile 50 mL centrifuge tube and delivered to the laboratory at room temperature within two hours. The study was approved by the Ethics Committees of the First Maternal and Child Health Hospital affiliated with Tongji University and the First People's Hospital of Chenzhou City, Hunan Province, China.

2. Collecting a Small Amount of Ovarian Tissues from the Follicular Aspirates

The follicular aspirates were filtered by using a cell strainer with 30 μm pore size and rinsed several times with sterile PBS buffer until there were no visible blood cells. The cell strainer was poured on a cell culture dish or centrifuge tube upside down, and the tissue masses adhered to the nylon strainer (the cell strainer with 30 μm pore size) were washed with sterile PBS buffer. The strainer was then placed under a dissecting microscope to see if it was clean and if there was any residue, the tissue masses can be collected with a tweezer. After centrifugation at 300 g for 5 minutes, the supernatant was discarded, and the tissue masses collected at the bottom of the centrifuge tube were used for subsequent experiments.

3. Results

Clinically, the shortage of ovarian specimens of patients restricts the basic research and clinical applications of FGSCs. Previous studies have found that follicular aspirates contain preantral follicles and mature oocytes can be obtained after in vitro culture.

Figure 2:
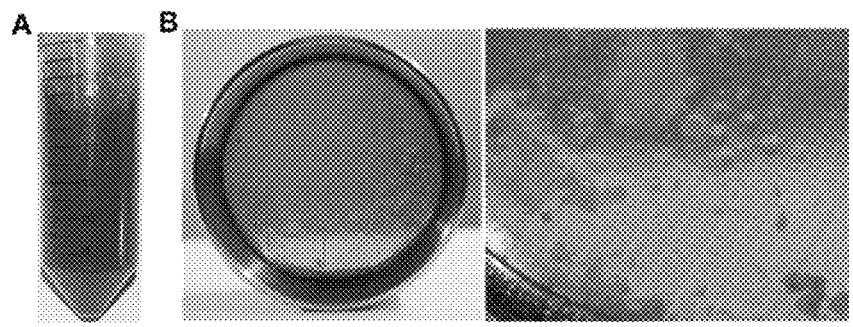
FIG. 2. Appearance and components of follicular aspirates.
A. The appearance of the follicular aspirates obtained from an IVF center; and
B. Tissues or cell masses adhered to the nylon strainer after filtration of the follicular aspirates over a 30-μm cell strainer. The right panel is an enlarged view of the boxed area.

The present inventors obtained discarded follicular aspirates from two IVF centers. Since follicular aspirates contain a variety of somatic cells, in order to remove these cell contaminations, the present inventors used a strainer with 30 μm pore size to remove these cells. During the operation, it was found that there were many tissues or cell masses on the strainer after filtration (FIG. 2).

Figure 3:
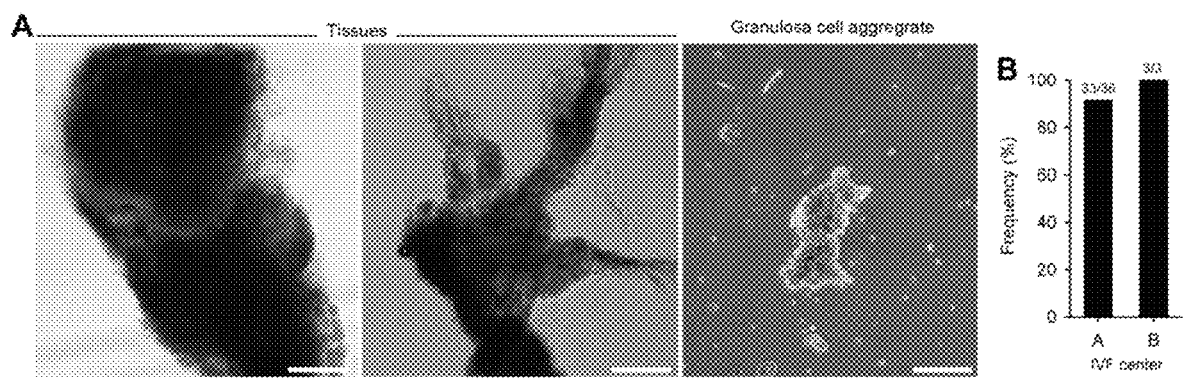
FIG. 3. The ovarian tissues and granular cell masses contained in the follicular aspirates.
A. Ovarian tissues (left and middle panels) and granular cell masses (right panel), which have different shapes and sizes, can be obtained from the follicular aspirates.
B. The proportion of the ovarian tissues obtained at two IVF centers.

These tissues or cell masses were observed under a microscope and they were found to contain small pieces of ovarian tissues and granular cell masses (FIG. 3A). Statistics found that ovarian tissues were detected in the samples derived from both IVF centers, and 91.7% and 100% of the total samples had ovarian tissues detected, respectively (FIG. 3B).

In summary, these results demonstrate that follicular aspirates contain a small amount of ovarian tissue masses.

Example 2

Separation and Identification of FGSCs from a Small Amount of Ovarian Tissues in the Follicular Aspirates 1. Preparing STO Feeder Layer STO cells were thawed, and then inoculated and cultured into a culture dish with DMEM (Life Technologies) culture medium containing the following components: 1 mM non-essential amino acids (NEAA; Life Technologies), 10% fetal bovine serum (Hyclone), and 6 mg/L penicillin (Sigma). When preparing the feeder layer, STO cells were treated with 10 μg/mL mitomycin C (Sigma) for 2-3 hours, washed several times with PBS, and then digested with trypsin into single cells which were inoculated on a 0.1% (w/v) gelatin-coated cell culture plate and incubated with STO culture medium.

2. Separating FGSCs

The ovarian tissue masses collected in the previous example were placed in PBS containing 1 mg/mL collagenase IV and then slowly shaken for 5 minutes in a water bath at 37° C. The solution was centrifuged at 300 g for 5 minutes, and then washed once with PBS buffer, and centrifuged again. PBS containing 0.5 mM EDTA and 0.05% trypsin was added to the centrifuge tube, and the centrifuge tube was slowly shaken for 2-3 minutes in a water bath at 37° C. After the cells were substantially dispersed, 10% fetal bovine serum was added to stop the action of trypsin. The solution was centrifuged at 300 g for 5 minutes and then the supernatant was carefully removed. The cells were resuspended by adding the culture medium and inoculated on the mitomycin C-inactivated feeder layer of STO single cells. The cells were cultured in a stem cell culture medium for two weeks and subjected to magnetic bead sorting. During magnetic bead sorting, goat anti-rabbit IgG-conjugated magnetic beads (Dynabeads, 112.03 D) were incubated with the rabbit polyclonal DDX4 antibody (Abcam; ab13840) according to the instructions, and then the coated magnetic beads were incubated with the cells. The positive cells were sorted by using a magnetic bead rack.

3. Culturing FGSCs

The culture system of FGSCs requires the use of the inactivated STO feeder layer. The culture medium for FGSCs was MEMα containing the following components: 10% fetal bovine serum (Front), 1 mM sodium pyruvate (Sigma), 1 mM non-essential amino acids, 2 mM L-glutamine (Sigma), 0.1 mM β-mercaptoethanol (Sigma), 10 ng/mL human leukemia inhibitory factor (LIF; Santa Cruz Biotechnology, sc-4377), 10 ng/mL human epidermal growth factor (EGF; Peprotech, AF-100-15), 40 ng/mL human glial cell-derived neurotrophic factor (GDNF; Peprotech, 450-10), 10 ng/mL human basic fibroblast growth factor (bFGF; Peprotech, AF-100-18B) and 6 mg/L penicillin.

Magnetic beads-sorted cells (approximately 500 cells) were inoculated into a well of a 24-well plate containing the STO feeder layer, and the stem cell culture medium was added for culture.

The culture medium was exchanged every 2-3 days, and the cells were passaged at a ratio of 1:1 to 1:3 with dispase II (Roche) every 5-8 days. All cells were cultured in a constant incubator containing 5% $CO_2$ at 37° C.

4. Immunofluorescence Staining

The cells were fixed with 4% PFA at room temperature for 20 minutes, washed twice with PBS, and blocked with a blocking solution (PBS containing 10% goat serum) at 37° C. for 10 minutes. The cells were then incubated overnight at 4° C. in one of the following diluted primary antibodies [1:500 diluted DDX4 antibody (Abeam; ab13840); 1:100 diluted OCT4 antibody (Santa Cruz Biotechnology; sc-9081); 1:100 diluted IFITM3 antibody (Abcam; ab15592); 1:100 diluted BLIMP-1 antibody (ABGENT Crown; AP14521a); 1:100 diluted DAZL antibody (Abcam; ab128238); or 1:150 diluted BrdU (Thermo scientific; clone BRD.3)].

The next day, the cells were washed twice with PBS, and then incubated in a 1:150 diluted secondary antibody [TRITC-conjugated goat anti-rabbit IgG (ProteinTech, recognizing DDX4, OCT4, IFITM3, BLIMP-1 and DAZL) or goat anti-mouse IgG (ProteinTech, recognizing BrdU)] at 37° C. in dark for 30 minutes, and then counterstained with DAPI for 20 minutes. A fluorescent anti-quencher was added and photos were taken.

5. RT-PCR

Total RNAs were extracted from the tissues and cells and reverse-transcribed using the HiScript® II Q RT SuperMix (+ gDNA wiper) kit (Vazyme, R223-01) according to the instructions. RT-PCR was performed using Taq polymerase (Takara, R10T1M) with primers shown in Table 1 for 35 cycles. The PCR-amplified GAPDH gene was used as an internal reference. Electrophoresis was performed using 2% agarose gel and the DNA bands were stained with ethidium bromide (EB). The PCR products were obtained and sequenced to determine whether the bands were the corresponding genes.

TABLE 1

PCR primers used for analyzing the gene expressions in human FGSCs and ovarian tissues

| Gene | Accession number | Product length (bp) | Primer sequence (5'→3')[#] | SEQ ID NO: |
|---|---|---|---|---|
| DDX4 | NM_024415 | 139 | F: CGTTGAAATTCTGCGAAACA | 1 |
| | | | R: TCTCTGTTCCCGATCACCAT | 2 |
| IFITM3 | NM_021034 | 214 | F: ACCATGTCGTCTGGTCCCTGT | 3 |
| | | | R: AGCACTGGGATGACGATGAGCAGA | 4 |
| OCT4 | NM_002701 | 564 | F: TGAGGGCGAAGCAGGAGT | 5 |
| | | | R: TGGCGCCGGTTACAGAA | 6 |
| STELLA | NM_199286 | 168 | F: GTTACTGGGCGGAGTTCGTA | 7 |
| | | | R: TGAAGTGGCTTGGTGTCTTG | 8 |

TABLE 1-continued

PCR primers used for analyzing the gene expressions in human FGSCs and ovarian tissues

| Gene | Accession number | Product length (bp) | Primer sequence (5'→3')# | SEQ ID NO: |
|---|---|---|---|---|
| DAZL | NM_001190811 | 163 | F: GCCCACAACCACGATGAATC | 9 |
| | | | R: CGGAGGTACAACATAGCTCCTTT | 10 |
| BLIMP-1 | NM_001198 | 300 | F: GGGTGCAGCCTTTATGAGTC | 11 |
| | | | R: CCTTGTTCATGCCCTGAGAT | 12 |
| STRA8 | NM_182489 | 220 | F: ACTCTCAGTCTGATCTCATAGCC | 13 |
| | | | R: TACCAAGGGGAGGAACCATTC | 14 |
| SYCP3 | NM_001177949 | 136 | F: TCAGAGCCAGAGATTGAAAACA | 15 |
| | | | R: TTGCAACATAGCCATTTCTTTTT | 16 |
| C-KIT | NM_000222 | 291 | F: GGCATGCTCCAATGTGTGG | 17 |
| | | | R: GGTGTGGGGATGGATTTGC | 18 |
| FIGLA | NM_001004311 | 155 | F: GGCAAGACAGCTGTCAAGA | 19 |
| | | | R: TTGGGGAGATAATTTCAGTCGT | 20 |
| GDF9 | NM_005260 | 118 | F: ATGGCACGTCCCAACAAATTC | 21 |
| | | | R: ACTCAGCACTAGCAGCAATCT | 22 |
| GJA4 | NM_002060 | 119 | F: TGCAAGAGTGTGCTAGAGGC | 23 |
| | | | R: ACAAAGCAGTCCACGAGGTAG | 24 |
| ZP1 | NM_207341 | 219 | F: CGCCATGTTCTCTGTCTCAA | 25 |
| | | | R: CGTTTGTTCACATCCCAGTG | 26 |
| ZP2 | NM_003460 | 245 | F: GCCTCCCAGGACCCATTCTC | 27 |
| | | | R: CAGGTAGCAGATGGAGCCTA | 28 |
| ZP3 | NM_001110354 | 273 | F: AGCAGGACCCAGATGAACTCAACA | 29 |
| | | | R: AAGCCCACTGCTCTACTTCATGGT | 30 |
| NANOG | NM_024865 | 215 | F: CAGAAGGCCTCAGCACCTAC | 31 |
| | | | R: CTGTTCCAGGCCTGATTGTT | 32 |
| SOX-2 | NM_003106 | 437 | F: ATGCACCGCTACGACGTGA | 33 |
| | | | R: CTTTTGCACCCCTCCCATTT | 34 |
| REX-1 | NM_174900 | 306 | F: CAGATCCTAAACAGCTCGCAGAAT | 35 |
| | | | R: GCGTACGCAAATTAAAGTCCAGA | 36 |
| GAPDH | NM_002046 | 210 | F: GACATCAAGAAGGTGGTGAAGC | 37 |
| | | | R: GTCCACCACCCTGTTGCTGTAG | 38 |

F: forward primer; and R: reverse primer.

6. Cryopreserving and Resuscitating FGSCs

FGSCs were digested with trypsin, mixed with FGSC culture medium containing 10% DMSO (Sigma) and then placed in a 2 ml cryotube. The cryotube was placed in an isopropanol cryopreserving box (Mr. Frosty) and placed in a freezer at −80° C. overnight. The next day, the cryotube was placed in liquid nitrogen for long-term storage. For cell resuscitation, the cryotube was quickly placed and thawed in a water bath at 37° C. The cryotube was centrifuged at 300 g for 5 minutes and the supernatant was discarded. The cells were cultured in the FGSC culture medium.

7. Results

Figure 4:
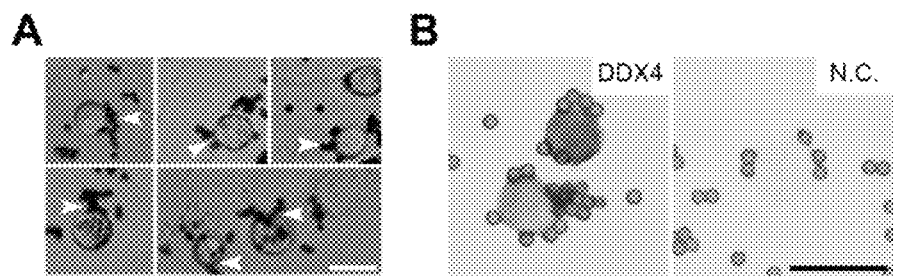
FIG. 4. Female germline stem cells (FGSCs) separated from the follicular aspirates.
A. DDX4$^+$ cells sorted after a small amount of ovarian tissues in the follicular aspirates are digested and cultured in vitro for 2 weeks. White arrows indicate magnetic beads.
B. Immunocytochemical staining is used to confirm that the sorted cells are DDX4$^+$ cells.

The small amount of ovarian tissues described above were digested into single cells using two-step enzymatic digestion, and then the cells were inoculated on the mitomycin C-inactivated STO feeder layer and cultured in vitro. Two weeks later, magnetic bead sorting was performed using a C-terminal DDX4 antibody. The sorted cells were round or oval, with a diameter of 8-15 μm and a relatively large nucleus, and each cell was bound with 1-3 unequal magnetic beads around (FIG. 4A).

In order to identify whether these cells express the germline markers, the present inventors immunocytochemically detected the expression of DDX4. As shown in FIG. 4B, the sorted cells express DDX4.

Figure 5:
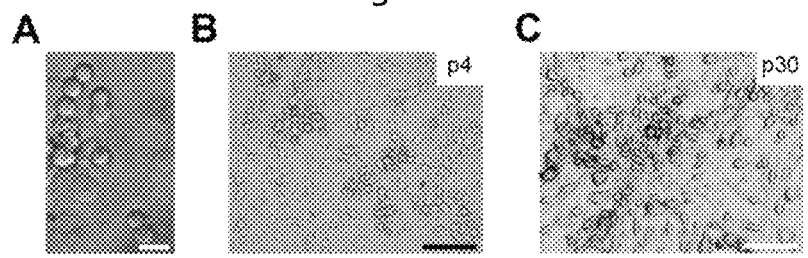
FIG. 5. The morphology of FGSCs cultured in vitro.
A. FGSCs in the division stage.
B. The cell morphology of the fourth generation (p4) FGSCs.
C. The cell morphology of the 30th generation (p30) FGSCs.

The DDX4$^+$ cells were subsequently inoculated on the feeder layer for subsequent culture. Early in the culture, the present inventors could observe the aggregated growth of the cells, and that the cells grew slowly in clusters (FIG. 5A). The cells then grew quickly and stably, requiring one passage every 5-7 days (FIG. 5B). With culturing according to the procedure described above, the cells could grow stably after cryopreserving-thawing (FIG. 5C).

Figure 6:
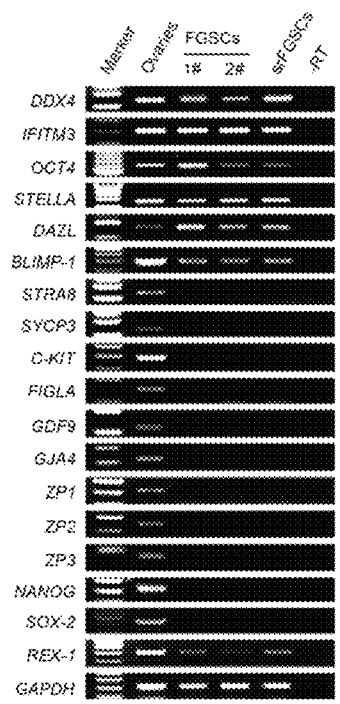
FIG. 6. RT-PCR analysis of human ovarian tissues (28 years old), FGSC cell lines (1# and 2#) and FGSCs obtained from the surgically removed ovaries (srFGSCs).

The present inventors detected the gene expressions of two FGSC cell lines (1# and 2#) and FGSC cell lines obtained from surgically removed ovaries (srFGSCs) by RT-PCR at the mRNA level, in order to determine the cell characteristics. The expressions of DDX4, IFITM3, OCT4, STELLA, DAZL, BLIMP-1, STRA8, SYCP3, C-KIT, FIGLA, GDF9, GJA4, ZP1, ZP2, ZP3, NANOG, SOX2, and REX-1 in the above-mentioned cells/tissues were detected by using the ovarian total cDNAs of a 28-year-old woman of childbearing age (a patient with ovarian cysts) as a positive control and the non-reverse-transcribed mRNA as a negative control. As shown in FIG. 6, these two FGSC cell lines (1# and 2#) and srFGSCs express DDX4, IFITM3, OCT4, STELLA, DAZL, BLIMP-1, and REX-1. However, they do not express the meiosis specifically expressed genes STRA8 and SYCP3; the oocyte-associated genes C-KIT, FIGLA, GDF9, GJA4, ZP1, ZP2, and ZP3; and the pluripotent genes NANOG and SOX2. Therefore, it can be determined that the cell lines established by the present inventors are undifferentiated germline stem cells.

Figure 7:
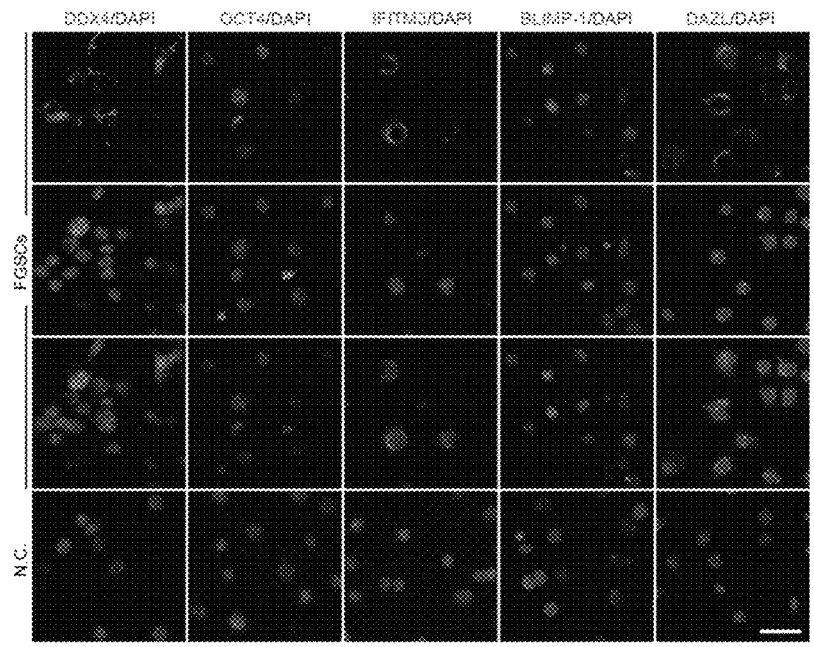
FIG. 7. Immunofluorescence staining of DDX4, OCT4, IFITM3, BLIMP-1 and DAZL proteins in the FGSC cell lines.

Subsequently, the present inventors detected germline cell markers at the protein level. As shown in FIG. 7, FGSCs express the germline-specific markers DDX4, OCT4, IFITM3, BLIMP-1, and DAZL proteins. It is confirmed at the protein level that the cell lines cultured by the present inventors are of germ cell origin.

Figure 8:
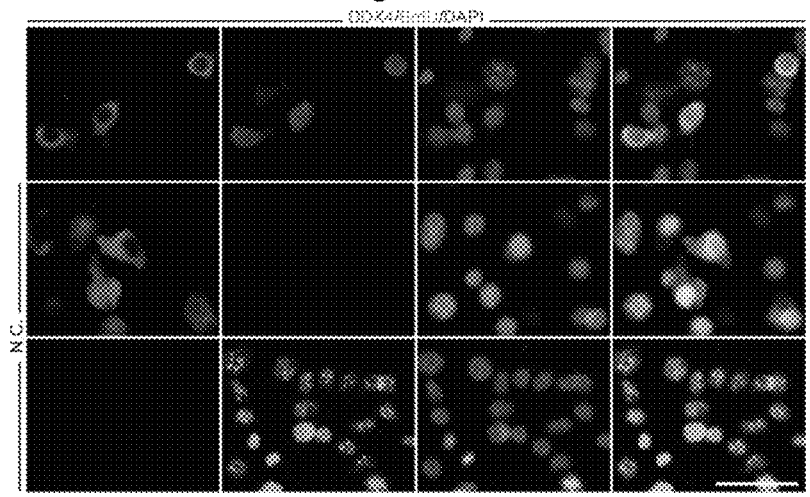
FIG. 8. Dual immunofluorescence staining of BrdU and DDX4 in the FGSC cell lines.

BrdU (5-bromodeoxyuridine) is an analogue of thymidine T, and may be incorporated into the genome during DNA replication. The antibody antigen reaction can be used to detect its incorporation into cells, thereby reflecting its proliferative capacity. DDX4 is a germ cell-specific marker. Proliferating germ cells can be identified by dual-labelled immunofluorescence cytochemistry with BrdU and DDX4. As shown in FIG. 8, the cultured cells have proliferation activity.

Figure 9:
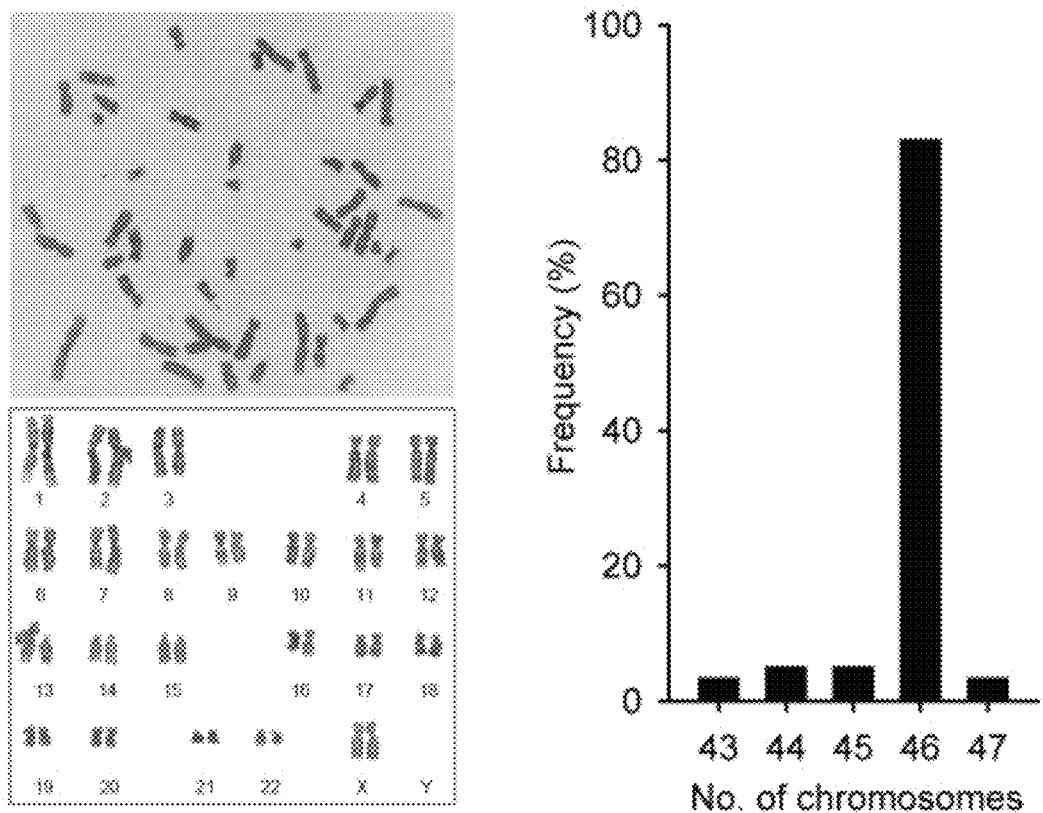
FIG. 9. G-banding karyotype analysis of FGSC cell lines, showing a normal karyotype (46, XX) and its proportion (right panel). n=59.

Then, the present inventors performed G-banding karyotype analysis on FGSCs to determine whether their karyotypes were normal. As shown in FIG. 9, 83% of FGSCs have 46 chromosomes and belong to diploid cells.

In summary, it is demonstrated that FGSCs can be obtained from follicular aspirates.

All the documents mentioned in the present invention are incorporated by reference in the present application, as if each document was incorporated by reference alone. In addition, it should be understood that after reading the above-mentioned teachings of the present invention, those skilled in the art would be able to make various modifications or amendments to the present invention, and these equivalents likewise fall within the scope defined by the appended claims of the present application.

The invention claimed is:

1. A method for separating female germline stem cells from follicular aspirates, comprising:
   (a) separating ovarian tissues and/or cell masses from the follicular aspirates and dispersing the ovarian tissues and/or cell masses to obtain single cells; and
   (b) inoculating and culturing the single cells obtained in step (a) on inactivated feeder layer cells, and sorting female germline stem cell marker-positive cells from the cultured cells.

2. The method of claim 1, further comprising:
   (c) subculturing the female germline stem cell marker-positive cells obtained in step (b) on feeder layer cells in a proliferation culture medium to expand female germline stem cells.

3. The method of claim 1, wherein step (a) comprises filtering the follicular aspirates through a cell strainer with a pore size of 30-100 μm, and collecting the ovarian tissues and/or cell masses retained on the cell strainer.

4. The method of claim 3, further comprising separating the ovarian tissues and/or cell masses retained on the cell strainer, and centrifuging the ovarian tissues and/or cell masses separated from the cell strainer.

5. The method of claim 1, wherein step (a) further comprises removing red blood cells from the ovarian tissues and/or cell masses prior to the dispersing step.

6. The method of claim 1, wherein in step (a), the cell dispersion is performed by using one or more enzymes selected from the group consisting of collagenase IV, trypsin, trypsin substitute, and Acutase.

7. The method of claim 1, wherein in step (b), the feeder layer cells include STO cells, MEF cells or SNL cells.

8. The method of claim 1, wherein the inactivated feeder layer cells in step (b) are mitomycin C-inactivated feeder layer cells; or the culture period on the feeder layer cells is 10-18 days in step (b).

9. The method of claim 1, wherein in step (b), an antibody specific to a female germline stem cell marker is conjugated to magnetic beads and incubated with the cells cultured on the feeder layer cells in order to sort the female germline stem cell marker-positive cells.

10. The method of claim 1, wherein the inactivated feeder layer cells are obtained as follows: the feeder layer cells are treated with mitomycin C, digested into single cells after washing, and inoculated on a gelatin-coated cell culture plate.

11. The method of claim 1, wherein the female germline stem cell marker includes DDX4 and/or IFITM3.

12. The method of claim 2, further comprising subculturing the female germline stem cell marker-positive cells obtained in step (b) on feeder layer cells in a stem cell culture medium.

* * * * *